United States Patent
Babaev (10) Patent No.: US 8,050,752 B2
(45) Date of Patent: Nov. 1, 2011

(54) METHOD OF TREATING LUMENS, CAVITIES, AND TISSUES OF THE BODY WITH AN ULTRASOUND DELIVERED LIQUID

(75) Inventor: Eilaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 1130 days.

(21) Appl. No.: 11/536,928

(22) Filed: Sep. 29, 2006

(65) Prior Publication Data

US 2008/0119779 A1  May 22, 2008

(51) Int. Cl.
*A61N 1/30* (2006.01)
*B05B 1/08* (2006.01)
*B05B 3/04* (2006.01)
*A61M 31/00* (2006.01)

(52) U.S. Cl. .................. 604/20; 239/102.1; 604/500
(58) Field of Classification Search .............. 604/19–22; 601/2–3; 239/102.1, 102.2
See application file for complete search history.

(56) References Cited

U.S. PATENT DOCUMENTS

| | | | |
|---|---|---|---|
| 4,767,402 A | 8/1988 | Kost et al. | |
| 4,961,018 A | 10/1990 | Akhter | |
| 4,982,730 A * | 1/1991 | Lewis, Jr. .................. | 601/2 |
| 5,405,614 A | 4/1995 | D'Angel et al. | |
| 5,415,629 A | 5/1995 | Henley | |
| 5,421,816 A | 6/1995 | Lipvoker | |
| 5,538,503 A | 7/1996 | Henley | |
| 5,658,247 A | 8/1997 | Henley | |
| 5,667,487 A | 9/1997 | Henley | |
| 5,830,192 A * | 11/1998 | Van Voorhis .................. | 604/533 |
| 5,947,921 A | 9/1999 | Johnson et al. | |
| 6,041,253 A | 3/2000 | Kost et al. | |
| 6,104,952 A * | 8/2000 | Tu et al. .......................... | 604/20 |
| 6,190,315 B1 | 2/2001 | Kost et al. | |
| 6,234,990 B1 | 5/2001 | Rowe et al. | |
| 6,322,532 B1 | 11/2001 | D'Sa et al. | |
| 6,491,657 B2 | 12/2002 | Rowe et al. | |
| 6,601,581 B1 | 8/2003 | Babaev | |

(Continued)

FOREIGN PATENT DOCUMENTS

WO  9717933 A1  5/1997

(Continued)

OTHER PUBLICATIONS

Calhoun, Jason H. and Manring, M.M. Adult osteomyelitis. Infectious Disease Clinics of North America 2005; 19: 765-786.

(Continued)

Primary Examiner — Kevin C Sirmons
Assistant Examiner — William Carpenter (57) ABSTRACT

The present invention relates to a method of treating lumens, cavities, and tissues of the body with a liquid delivered with the use of ultrasound. Delivering a liquid with the use of ultrasound may be accomplished by utilizing a device comprising an ultrasound transducer, an ultrasound horn, a channel running at least partially through said horn, and a dampening grommet at the distal end of the horn (hereafter called the "delivery device"). The delivery device may further comprise a liquid supply emptying into said channel. Subjecting liquids within the horn of the delivery device to ultrasonic energy accelerates the liquid, thereby creating a higher velocity, low pressure liquid stream. Consequently, the method of the present invention enables the treatment of maladies deep within lumens, cavities, and tissues of the body. The method of the present invention may also be used for douching and/or cleaning lumens, cavities, and tissues of the body.

10 Claims, 6 Drawing Sheets

U.S. PATENT DOCUMENTS

| | | | |
|---|---|---|---|
| 6,623,444 B2 | 9/2003 | Babaev | |
| 6,916,296 B2 * | 7/2005 | Soring et al. | 601/2 |
| 6,923,790 B2 * | 8/2005 | Lal et al. | 604/151 |
| 6,964,647 B1 * | 11/2005 | Babaev | 604/22 |
| 7,201,167 B2 * | 4/2007 | Fink et al. | 128/203.12 |
| 7,431,704 B2 * | 10/2008 | Babaev | 601/2 |
| 2002/0138036 A1 * | 9/2002 | Babaev | 604/22 |
| 2002/0156400 A1 * | 10/2002 | Babaev | 601/2 |
| 2003/0153961 A1 * | 8/2003 | Babaev | 607/89 |
| 2003/0236560 A1 * | 12/2003 | Babaev | 607/50 |
| 2005/0229926 A1 | 10/2005 | Fink et al. | |
| 2006/0025716 A1 | 2/2006 | Babaev | |
| 2006/0173385 A1 | 8/2006 | Lidgren et al. | |
| 2006/0241470 A1 * | 10/2006 | Novak et al. | 600/459 |
| 2006/0241533 A1 * | 10/2006 | Geller | 601/4 |

FOREIGN PATENT DOCUMENTS

WO    WO 2004/093972    * 11/2004

OTHER PUBLICATIONS

Kaplan, Sheldon L. Osteomyelitis in children. Infectious Disease Clinics of North America 2005; 19: 787-797.

* cited by examiner

METHOD OF TREATING LUMENS, CAVITIES, AND TISSUES OF THE BODY WITH AN ULTRASOUND DELIVERED LIQUID

BACKGROUND OF THE INVENTION

1. Field of the Invention

The present invention relates to a method of treating lumens, cavities, and tissues of the body with a liquid delivered with the use of ultrasound.

2. Description of the Related Art

Various infections, conditions, ailments, and diseases (hereafter collectively referred to as "maladies") of the body are difficult to treat pharmacologically due to inaccessibility of the site of the malady to pharmacologically active compounds (commonly referred to as "drugs") such as, but not limited to, chemical compounds, chemicals, small molecules, proteins, genes, and/or any combination thereof. Such sites include body lumens and body cavities such as, but not limited to, the urethra, sinuses, vagina, uterus, outer ear, lungs, thoracic cavity, and colon, and poorly vasculated tissue such as, but not limited, to bones. Though commonly considered otherwise by those outside of the biological arts, lumens and body cavities are outside of the body. This somewhat paradoxical statement can best be understood by considering the path an orally taken drug travels to reach the urethra, a component of the urinary tract.

A pill containing the drug is first dissolved in the stomach and/or small intestine after being swallowed, thereby liberating small drug molecules. The small drug molecules are then carried into the cells forming the walls of the small intestine by transport molecules on the cells' surfaces. Alternatively the drug molecules may pass directly into the cells of the small intestine on their own by either diffusing through cellular membranes or passing through pores located within the cellular membranes. Once within the cells forming the walls of the small intestine, the drug molecules are transported by similar mechanisms into the patient's blood stream. The drug molecules then spread throughout the patient's entire blood stream where they are subjected to degradation and/or inactivation by various elements within the blood. The blood stream also transports the drug molecules to potential sites of degradation, inactivation, and/or excretion such as, but not limited to, the kidneys and liver. Despite dilution by wide spread distribution, inactivation, degradation, and/or excretion, some of the drug molecules reach areas of the blood stream adjacent to the urethra. However, to effectively treat a malady within the urethra, the drug must be taken out of the bloodstream by the cells forming the urethra and then deposited into the open space of the urethra. Drug molecules may also reach the urethra by excretion into the urine, which flows through the open space of the urethra. Unfortunately, the urine is not kept at a constant pH, and may become sufficiently acidic or basic as to inactivate and/or degrade the drug molecules.

With respect to maladies within poorly vasculated and/or perfused tissue, pharmacological treatment is limited by a poor blood supply. Most methods of drug delivery into the body rely upon the blood stream to deliver the drug molecules to the site of the malady to be treated. Consequently the amount of drug delivered is positively related to the amount of blood delivered to the site of the malady. Therefore, a location or tissue of the body that receives a diminished, reduced, compromised, or small supply of blood is less accessible to pharmacological treatment. Various medical devices and procedures have been developed to supplement pharmacological treatment of maladies located within lumens, open body cavities, and/or poorly perfused tissues.

Catheter drug delivery methods and devices have been developed to overcome the limitations of pharmacological treatment. Inserting catheters into lumens or body cavities and injecting a drug through or from the catheters gives pharmacologically active compounds access to the site of a malady. Running a catheter through a small or narrow body lumen, such as the urethra, can be uncomfortable for the patient. Inflicting injury while inserting the catheter can create serious complications such as allowing an infection on the inner wall of the lumen or body cavity to enter the blood stream, thereby spreading the infection throughout the body. Furthermore, finding the site of the malady to be treated, while inserting the catheter, can be difficult.

To get past the delivery limitations of drugs for the treatment of maladies within shallow lumens or cavities of the body, creams and other medical ointments have been developed. The cream or ointment is spread on the walls of the cavity with a finger, swab, or similar device. Though these creams and ointments can be effective, their use is generally not preferred by the patient as they can be messy, leak out, and are often unpleasant to apply.

Delivering drugs to open body cavities and/or lumens not sufficiently accessible as to permit the application of creams, such as the sinuses, has been accomplished with various spray and/or misting devices. Exemplar devices well known in the art are nasal sprays and inhalers. Generating a spray or mist through the use of pumps or aerosols, it is difficult to utilize nasal sprays and inhalers to deliver drugs deep within an open cavity. The difficulty in achieving deep drug delivery is due to the low pressure, low velocity sprays generated by these devices. Generation of the spray or mist is generally accomplished by pressurizing the drug to be delivered and then forcing the drug through a small orifice. As to avoid damaging tissue within the cavity or lumen into which the drug is to be delivered, low pressure is used to drive drug delivery. Because pressure is the only force driving drug delivery, the use of low pressure creates a low velocity spray limiting the depth of drug penetration. Consequently, it is difficult to deliver drugs from such devices to sites of maladies deep within body cavities or lumens.

Preserving the integrity of bones, particularly bone marrow, is critically important for maintaining patient health, because bones are the site of red and white blood cell synthesis. Maladies within the bones, such as leukemia and/or osteomyelitis, can result in anemia and a compromised immune system. Treating such conditions often involves painful surgery due to the inability of drugs to adequately penetrate bone tissue. In the case of leukemia, the patient is often treated with painful bone marrow transplants during which unhealthy bone marrow is replaced with healthy bone marrow from a donor. With respect to the treatment of osteomyelitis, surgical debridement is the principal therapy. During the surgery, the bone is opened and the diseased tissue is scrapped away. The debridement procedure often leaves a large bony defect (dead space). Poorly vascularized, the presence of a dead space predisposes the patient to persistent infections. Consequently, dead bone tissue must be replaced with durable vascularized tissue. Debridement may need to be followed by stabilization such as external or internal fixation. Internal fixation devices often become infected resulting in painful complications to the patient. External fixation is labor intensive and requires an extended period of treatment averaging 8.5 months.

Ultrasound drug delivery devices have been developed in efforts to overcome some of the limitations of drug therapy. U.S. Pat. No. 5,405,614 to D'Angelo et al., U.S. Pat. No.

5,415,629 to Henley, U.S. Pat. No. 5,421,816 to Lipkovker, U.S. Pat. No. 5,538,503 to Henley, U.S. Pat. No. 5,658,247 to Henley, U.S. Pat. No. 5,667,487, to Henley, U.S. Pat. No. 5,947,921 to Johnson et al., U.S. Pat. No. 6,041,253 to Kost et al., U.S. Pat. No. 6,190,315 to Kost et al, U.S. Pat. No. 6,234,990 to Roe et al., U.S. Pat. No. 6,322,532 to D'Sa et al., and U.S. Pat. No. 6,491,657 to Rowe et al describe transdermal ultrasound drug delivery devices utilizing ultrasonic energy to drive a drug across the patient's skin. However, delivering drugs to deep tissue such as, but not limited to, bone marrow is difficult to accomplish with these devices. U.S. Pat. No. 6,601,581 to the present inventor describes an ultrasound inhaler utilizing ultrasonic energy to create a fine drug mist. Though effective at delivering drugs to the lungs and bronchia, this device is incapable of creating a spray of sufficient velocity to enable drug delivery deep within lumens and cavities of the body.

Though drugs are often effective in treating various maladies of the body, they are not always necessary. Many maladies of the body can be treated simply by washing and/or flushing the affected area. Washing and/or flushing with simple, drug free fluids such as, but not limited to, saline or water has the benefit of avoiding the various side effects and complications drugs may possess. Unfortunately, the practicality of washing and/or flushing body cavities, body lumens, and poorly perfused tissues is hindered, as is drug delivery, by the lack of devices capable of delivering a liquid deep into the affected lumens, cavities, and poorly perfused tissues.

The difficulty in achieving therapeutically effective drug concentrations or permit the washing and/or flushing of body lumens, body cavities, and poorly perfused tissues with present devices and traditional routes of administrations creates a need for a new method of treating body lumens, body cavities, and poorly perfused tissues.

SUMMARY OF THE INVENTION

The present invention relates to a method of treating lumens, cavities, and tissues of the body with a liquid delivered with the use of ultrasound. Delivering a liquid with the use of ultrasound may be accomplished by utilizing a device comprising an ultrasound transducer, an ultrasound horn, a channel running at least partially through said horn, and a dampening grommet at the distal end of the horn (hereafter called the "delivery device"). The delivery device may further comprise a liquid supply emptying into said channel. Subjecting liquids within the horn of the delivery device to ultrasonic energy accelerates the liquid, thereby creating a higher velocity, low pressure liquid stream. Consequently, the method of the present invention enables the treatment of maladies deep within lumens, cavities, and tissues of the body. The method of the present invention may also be used for douching and/or cleaning lumens, cavities, and tissues of the body.

Treating maladies of lumens, cavities, and/or tissues of the body with the method of the present invention entails first selecting an appropriate liquid. Selecting a liquid comprising a pharmaceutically active compound, or drug, with properties known or believed to treat the malady present may be advantageous. Alternatively, the liquid chosen may possess properties ideal for washing the lumen, cavity or tissue of the body to be treated (hereafter referred to as the "treatment area") of accretions, contaminants, infectious microbes, bacteria, funguses, impacted matter, dirt, debris, necrotic tissue, and/or other undesirable elements. Choosing a liquid capable of coupling the inner channel of the delivery device's horn with the treatment area as to allow for the transmission of ultrasonic energy released into the inner channel of the horn to the treatment area may also prove advantageous. The coupled ultrasonic energy may induce cavitations within the treatment area. The coupled ultrasonic energy may help to remove undesirable elements from the treatment area, dissolve accretions, promote the growth of healthy tissue within the treatment area, retard the growth of and/or kill unwanted tissue within the treatment area, retard the growth of and/or kill infectious microbes within the treatment area, enhance the entry of drugs into cells within and in the vicinity of the treatment area, and/or provide other positive healing benefits. The liquid chosen may possess all or some of the above mentioned properties.

The method of the present invention may also be used for preventative purposes. For instance, the method of the present invention may be used to wash the treatment area as to prevent and/or lessen the likelihood of developing a malady within the treatment area. Utilizing the method of the present invention to deliver liquids comprising vitamins, minerals, drugs, and/or other elements known and/or believed to have a positive effect on the treatment area may also help to preserve proper functioning of the treatment area and prevent the development of maladies therein. Preventing biological processes from occurring within the treatment area, such as, but not limited, ovulation, fertilization, and/or implantation, may also be accomplished by using the method of the present invention to deliver to the treatment area liquids possessing properties known and/or believed to retard the undesired processes. Conversely, inducing the occurrence of wanted biological processes, such as, but not limited, bowel movement, immune suppression, histamine inhibition, and/or bronchial dilation, may be accomplished by using the method of the present invention to deliver to the treatment area liquids possessing properties known and/or believed to promote the desired processes.

Once a liquid has been chosen, it should be loaded into a liquid supply, if present within the delivery device, or the channel within the ultrasound horn of the delivery device. If a liquid supply is utilized, it may be a syringe, a pump, a reservoir with a gravity feed, a pipette, and/or similar devices capable of dispensing a fluid into the channel of the ultrasound horn. Utilizing a liquid supply capable of delivering a set and/or predetermined amount of liquid or otherwise capable of indicating or monitoring the amount of liquid delivered allows those utilizing the method of the present invention to monitor and/or dose the amount of liquid delivered. The liquid supply may be coupled to the ultrasound horn by a flexible hose. Dampening, preventing, and/or lessening the transmission of vibrations from horn to the liquid supply, a flexible hose prevents needles and/or delicate tips of the liquid supply from breaking and/or shearing during operation.

Prior to liquid delivery, the treatment area must be made accessible if it is not already so. An accessible treatment area is one comprising a naturally occurring or a created external orifice and/or externally accessible orifice leading into it. If the orifice leading into the treatment area comprises a sore or wound created as a result of the malady to be treated, it is considered a naturally occurring orifice. If the treatment area is inaccessible, an orifice should be created. The creation of secondary orifices allows for the delivery of the chosen liquid from multiple sites into the treatment area. Delivering liquid from multiple orifices may provide a more uniform delivery of the chosen liquid into the treatment area. Alternatively, secondary orifices may provide a point of egress for the delivered liquid enabling the drainage of the delivered liquid and/or fluids within the treatment area, thereby allowing for the evacuation of liberated undesirable elements from the treatment area. The orifice leading into the treatment area, whether naturally occurring or created, may be reinforced by the implantation of cannula into the orifice as to prevent closure of the orifice.

Having chosen an appropriate liquid, prepared the liquid supply and, if necessary, the orifice leading into the treatment area, a person utilizing the method of the present invention then chooses an appropriate dampening grommet for the delivery device. Selecting an appropriate grommet requires consideration of the orifice extending into the treatment area. The distal end of the grommet chosen may possess an outer perimeter sufficiently small as to allow at least a portion of the grommet to be comfortably inserted into the orifice. Alternatively, the outer perimeter of the chosen grommet's distal end could be sufficiently large as to allow the grommet to encompass the orifice when pressed against the patient's body. Incorporation of a second channel within the grommet allows for the drainage of the delivered liquid and/or fluids from the treatment area; enabling the evacuation of liberated undesirable elements from the treatment area. The selection of the grommet may also occur before or simultaneously with the selection of the appropriate liquid. At least a portion of the grommet must be capable of dampening, lessening, and/or preventing the transmission of vibrations from the horn to patient and/or orifice. Dampening, lessening, and/or preventing the transmission of vibrations, the dampening grommet prevents and/or lessens the occurrence of injuries to the patient, such as, but not limited to, ultrasonic burns and/or tissue tearing.

After having chosen and attached the dampening grommet, a seal is formed between the grommet and an orifice leading into the treatment area. The transducer is then activated. If a liquid supply is being utilized, the liquid chosen is delivered into the channel within the ultrasound horn of the delivery device. As the liquid passes through the channel, the liquid becomes accelerated by ultrasonic energy and is ejected from the distal end of the grommet, into the treatment area, as a higher velocity liquid stream. If a liquid supply is not being used, the chosen liquid is then expelled from the channel within the horn by the ultrasonic energy emanating from the horn into the channel and is injected into the treatment area.

An aspect of the present invention is to provide for the delivery of liquids into tissues, lumens, and/or cavities of the body.

Another aspect of the present invention may be to allow washing of tissues, lumens, and/or cavities of the body.

Another aspect of the present invention may be delivering potentially therapeutic ultrasonic energy into tissues, lumens, and/or cavities of the body.

Another aspect of the present invention may be to allow for the treatment of maladies of tissues, lumens, and/or cavities of the body.

Another aspect of the present invention may be to prevent biological processes from occurring within tissues, lumens, and/or cavities of the body.

Another aspect of the present invention may be to promote the occurrence of biological processes within tissue, lumens, and/or cavities of the body.

Another aspect of the present invention may be to preserve proper functioning of tissues, lumens, and/or cavities of the body.

Another aspect of the present invention may be the removal of undesirable elements from tissues, lumens, and/or cavities of the body.

These and other aspects of the invention will become more apparent from the written descriptions and figures below.

BRIEF DESCRIPTION OF THE DRAWINGS

The present invention will be shown and described with reference to the drawings of preferred embodiments and clearly understood in detail. Like elements of the various embodiments depicted within the figures are equivalently numbered.

DETAILED DESCRIPTION OF THE DRAWINGS

Figure 1:
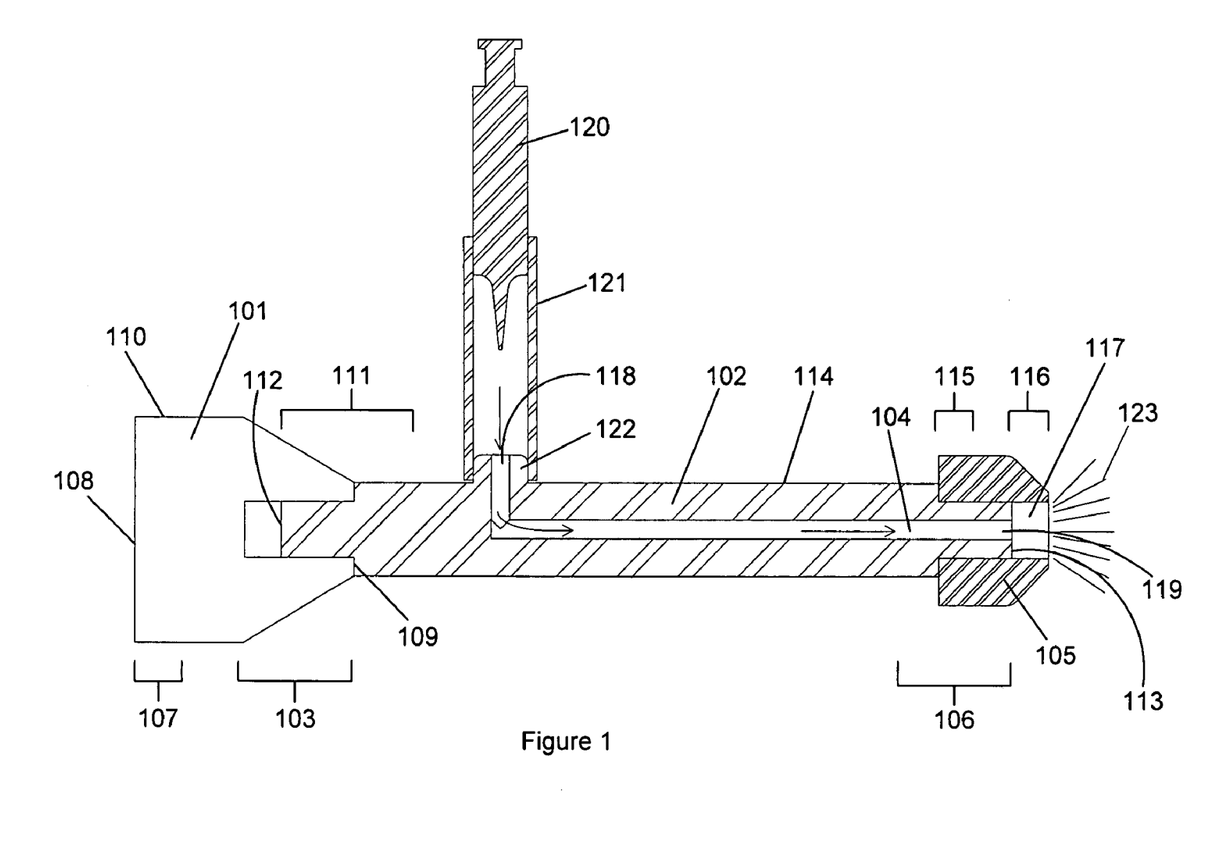
FIG. 1 depicts a cross sectional view of a delivery device that may be used when carrying out the method of the present invention.

Depicted in FIG. 1 is a cross sectional view of a delivery device that may be used when carrying out the method of the present invention. The liquid delivery device comprises an ultrasound transducer 101, an ultrasound horn 102 attached to the distal end 103 of said transducer 101, a channel 104 running at least partially through said horn 102, and a dampening grommet 105 attached to the distal end 106 of said horn. The transducer 101 contains a proximal end 107 including a proximal surface 108. Opposite its proximal end 107, transducer 101 has a distal end 103 including a distal surface 109. Extending between the proximal end 107 and the distal end 103 of the transducer 101 is a radial surface 110. The horn 102 contains a proximal end 111, including a proximal surface 112, attached to the distal end 103 of transducer 101. Opposite its proximal end 111, horn 102 has a distal end 106 including a distal surface 113. Extending between the distal end 106 and proximal end 111 of horn 102 is a radial surface 114. The dampening grommet 105 contains a proximal end 115 attached to the distal end 111 of horn 102. Opposite its proximal end 115, grommet 105 has a distal end 116. Extending from the proximal end 115 to the distal end 116 of grommet 105 is a channel 117, which is in communication with channel 104 within horn 102. Channel 104 contains a proximal end 118 originating in radial surface 114 of horn 102, and a distal end 119 opening within distal end 103 of horn 102.

The delivery device may further comprise at least one liquid supply 120 in communication with the proximal end 118 of channel 104. As depicted, channel 104 may begin within radial surface 114 at or near the proximal end 111 of horn 102. Alternatively, channel 104 may also run through at least a portion of transducer 101. In such an embodiment, channel 104 could be thought of as two channels in communication with one another. The first channel would be a channel originating in a surface of transducer 101, other than the distal surface 109, and extending at least partially through transducer 101 before opening into the second channel. The second channel would be a channel originating within proximal surface 109 of horn 102 and extending through horn 102 before opening at the distal end 106 of horn 102. The liquid supply depicted in FIG. 1 is a typical syringe. Other liquid supplies capable of dispensing a fluid into channel 104 may be similarly effective including, but not limited to, a pump, a reservoir with a gravity feed, and/or a pipette. A delivery device that may be utilized when carrying out the method of the present invention may further comprise a flexible hose 121 coupling liquid supply 120 to channel 104, as to prevent breaking and/or shearing of delicate tips and/or needles of the liquid supply chosen. As liquid dispensed into channel 104 by liquid supply 120 travels down channel 104, ultrasonic energy is emitted from horn 102 into the liquid, thereby accelerating the liquid's rate of flow. The liquid is then ejected from the distal end of grommet 105 as a higher velocity liquid stream 123.

Although an embodiment comprising only a single channel within the ultrasound horn and fluid supply is depicted within FIG. 1, there may be multiple channels within the horn and multiple liquid supplies. Incorporation of multiple liquid supplies connected to the same or multiple channels within the horn enables the delivery of multiple liquids to the treatment area during a single treatment session.

Figure 2:
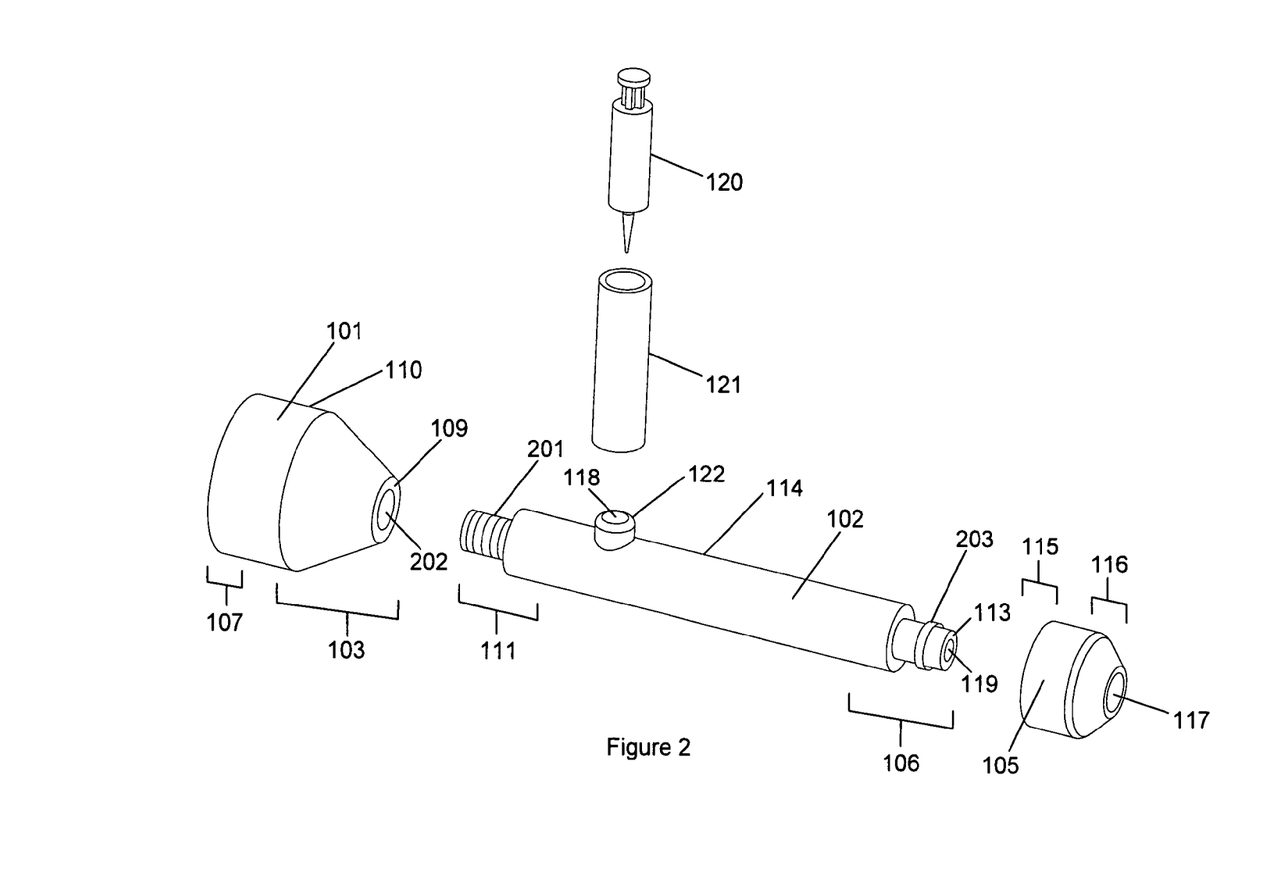
FIG. 2 depicts an exploded view of a delivery device that may be used when carrying out the method of the present invention.

FIG. 2 depicts an exploded view of a delivery device that may be used when carrying out the method of the present invention. As depicted, ultrasound horn 102 may be attached to transducer 101 by mechanical means. The mechanical means depicted comprise a threaded protrusion 201 on the proximal end 111 of the horn 102 with a matching threaded recess 202 in the distal end 103 of transducer 101. Other mechanical means may be used to attach horn 102 to transducer 101. Alternatively, horn 102 and transducer 101 may be formed as a solid piece or constructed from two separate pieces permanently attached by, but not limited to, welding. In yet another alternative embodiment, horn 102 and transducer 101 may be permanently or temporarily attached by adhesives. The means chosen to attach horn 102 to transducer 101 must allow for the transmission of vibrations generated in transducer 101 to horn 102 and prevent separation of horn 102 from transducer 101 during operation. Ridge 203 at the distal end 106 of horn 102 fits into a recess (not visible) within the inside surface of dampening grommet 105.

Figure 3:
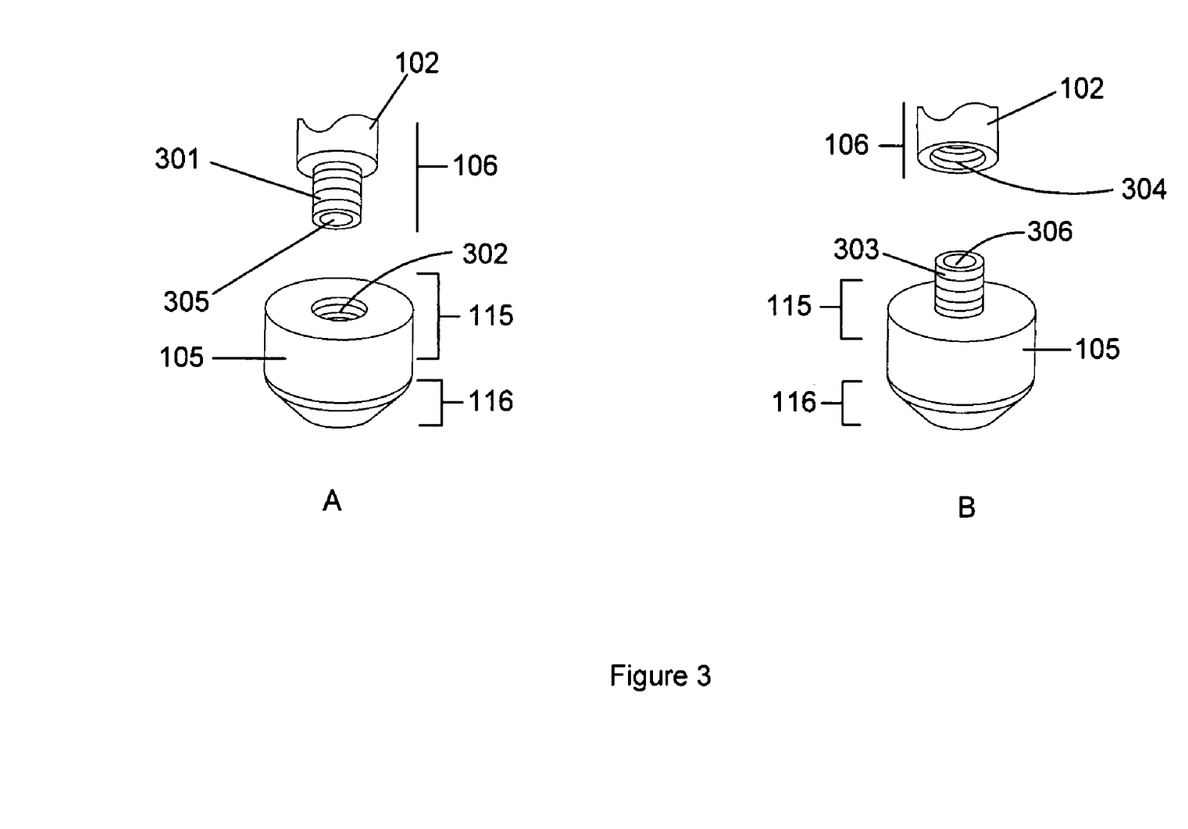
FIG. 3 is an illustration of alternative means of attaching the dampening grommet to the ultrasound horn when practicing the method of the present invention.

Other mechanical means, such as, but not limited to, a corresponding threaded protrusion and recess, may be used to attach dampening grommet 105 to horn 102, as depicted in FIGS. 3A and 3B. As depicted in FIG. 3A, a threaded protrusion 301 placed at the distal end of horn 102 is received by a threaded portion 302 within channel 117 at the proximal end 115 of grommet 105. Depicted in FIG. 3B is an alternative embodiment in which threaded protrusion 303 at the proximal end 115 of grommet 105 is received by threaded recess 304 at the distal end 106 of horn 102. As to permit the flow of liquid, it may be desirable for the threaded protrusions 301 and 303 to comprise a channel 305 and 306, respectively, running through them. Likewise, it may be desirable for the threaded recess 304 to be continuous with channel 104 within the ultrasound horn 102.

Alternatively, dampening grommet 105 may be attached to ultrasound horn 102 by adhesives. Other means of attaching grommet 105 to horn 102 may be utilized, provided the means chosen prevents the separation of horn 102 from grommet 105 during operation.

Returning to FIG. 2, port 122 located at the proximal end 118 of a channel 104 is a point of attachment for flexible hose 121. Though the port 122 is depicted as a raised protrusion, other means of attaching hose 121 to a channel 104 running through horn 102, such as, but not limited, a recess into which hose 121 may be inserted and/or adhesives, may be equally effective, provided they prevent the separation of hose 121 from the channel 104 during operation.

As to prevent the premature discharge of liquid from the liquid supply to a channel within the ultrasound horn, a valve may be placed between the liquid supply and the channel. Similarly, to prevent the premature discharge of liquid from the channel within the ultrasound horn into the treatment area a valve may be placed at or near the proximal end of the channel and/or within the dampening grommet.

Ultrasound horn 102 emits into channel 104 within it ultrasonic energy when induced to vibrate by transducer 101 at a frequency between approximately 15 kilohertz and approximately 40 megahertz. The amplitude of the induced ultrasonic vibrations should be approximately at least 1 micron. The preferred low frequency range of the induced ultrasonic vibrations is approximately 15 kilohertz to approximately 200 kilohertz, with a recommended frequency of approximately 20 kilohertz to approximately 60 kilohertz. The preferred low frequency amplitude ranges from approximately 15 microns to approximately 250 microns, with a recommended amplitude of approximately 50 microns. The preferred high frequency range of the induced ultrasonic vibrations is approximately 1 megahertz to approximately 20 megahertz, with a recommended frequency of approximately 1 megahertz to approximately 2 megahertz. The preferred high frequency amplitude ranges from approximately 1 micron to approximately 10 microns, with a recommended amplitude of approximately 5 microns.

The ultrasound transducer, depicted in FIGS. 1 and 2 as element 101, may be driven by a generator, which provides the power and signal that drives the transducer. The generator may be a separate unit and/or integral with the transducer. The generator may be powered by an external power supply, such as, but not limited, a traditional wall outlet. The generator may also have an internal power supply, such as, but not limited to, a battery.

The distal end of the dampening grommet should be sized to fit within and form a relative seal against the orifice leading into the treatment area. Alternatively, the distal end of the dampening grommet may be sized as to encompass the orifice leading into the treatment area and form a seal against the patient's body. Furthermore, the dampening grommet should be constructed and/or configured as to dampen, prevent, and/or lessen the transmission of vibrations from the ultrasound horn to the patient's body (hereafter referred to as "blocking the transmission of vibrations"). Blocking the transmission of vibrations may be achieved by constructing at least a portion the dampening grommet from rubber, plastic, silicon, and/or other compounds capable of absorbing, preventing, lessening, and/or dampening the transmission vibrations (hereafter referred to as "dampening properties"). The portion of the dampening grommet constructed from compounds possessing dampening properties should be positioned as to separate portions the grommet not constructed from such compounds. Alternatively the portion of the dampening grommet constructed from a compound possessing dampening properties may be at the proximal end of the grommet as to block the transmission of vibrations from the ultrasound horn to the distal end of the grommet. Constructing the distal end of the dampening grommet from a compound possessing dampening properties may also be effective. Alternatively, the dampening grommet may be configured such that at least a portion of it is mechanically capable of blocking the transmission of vibrations from the ultrasound horn to the patient (hereafter referred to as "mechanical dampening properties"). Such mechanical configurations may comprise, but are not limited to, a dashpot, a coil spring, a leaf spring and/or any combination thereof. When a configuration with mechanical dampening properties is employed, the use of compounds with dampening properties may not be needed. When the device is to be inserted through one lumen and/or open cavity of the body as to access an orifice leading into the treatment area, such as, but not limited to, when passing through the vagina to access the uterus, the dampening grommet should be constructed and/or configured as to protect the lumen and/or cavity through which it is passed from vibrations emitted from the ultrasound horn and/or transducer.

Figure 4:
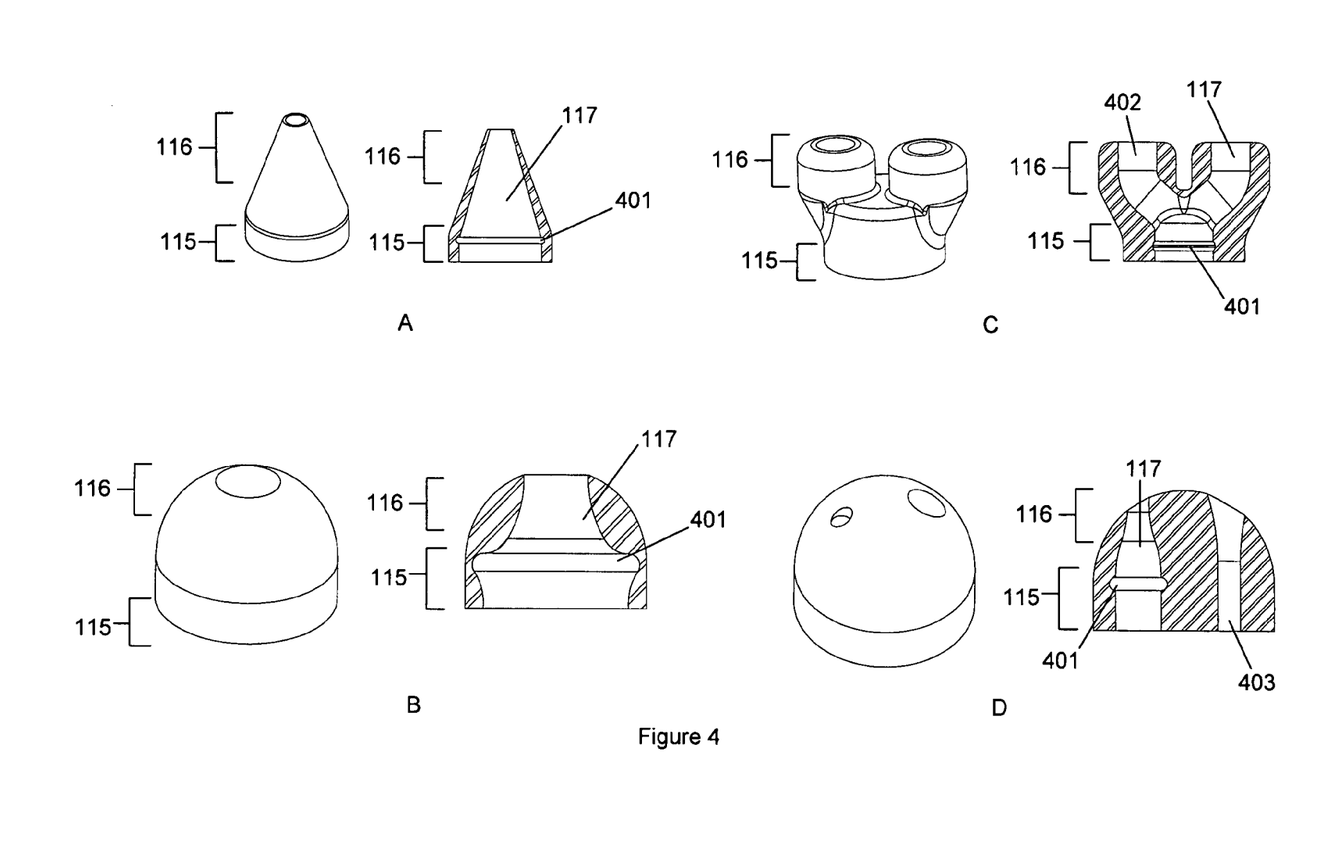
FIG. 4 depicts exemplar configurations of dampening grommets for use with a delivery device when carrying out the method of the present invention.

Depicted in FIG. 4 are exemplar configurations of dampening grommets for use with a delivery device when carrying out the method of the present invention. Though only a few specific exemplars are depicted, many configurations are possible.

Consequently, the configurations depicted in FIG. 4 and described in detailed below are meant only to be illustrative and non-limiting. FIGS. 4A, B, C, and D depict exemplar configurations of a dampening grommet completely constructed from a compound possessing dampening properties. FIG. 4A depicts an external and cross-sectional view of a dampening grommet possessing a needle like configuration. Capable of fitting into small orifices, a needle like configuration is ideally suited for delivering liquids into treatment areas accessible through narrow orifices such as, but not limited to, the urethra, a sore and/or wound. The needle like grommet depicted in FIG. 4A, like all dampening grommets, contains channel 117 running from the distal end 116 to the proximal end 115 of the grommet. Recess 401, located within channel 117, receives a ridge located on the distal end of the ultrasound horn and thereby mechanically secures the grommet to the horn. As described above, other means of attaching the horn to the grommet may be equally effective. FIG. 4B depicts an external and cross-sectional view of a dampening grommet well suited for liquid delivery into treatment areas accessible by way of an intermediate or large orifice such as, but not limited to, the nostrils, anus, and/or vagina. FIG. 4C depicts an external and cross-sectional view of a dampening grommet with a double rounded distal end 116 and a second channel 402 branching off of internal channel 117 and opening at the distal end 116 that is well suited for delivering liquids into the sinuses through both of the patient's nostrils simultaneously. FIG. 4D depicts an external and cross-sectional view of a dampening grommet with a rounded configuration further comprising a second channel 403 well suited for douching a treatment area. Unlike channel 117, liquids from the liquid supply are not fed through channel 403. Rather channel 403 serves as a point of evacuation for liquids delivered to and/or fluids within the treatment area. Channel 403 may be connected to a collection reservoir and/or other means capable of collecting and containing spent liquids and/or discharged fluids.

Figure 5:
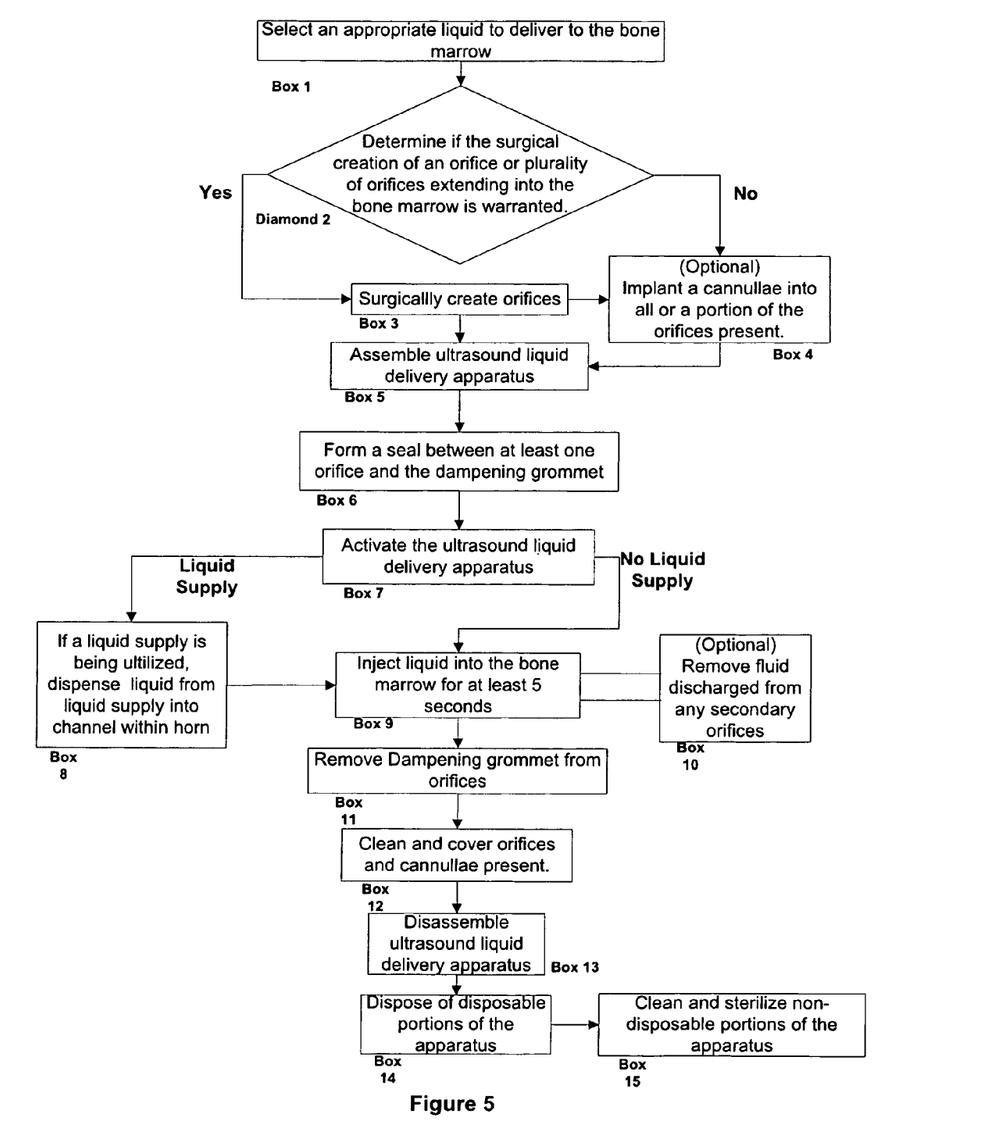
FIG. 5 contains a flow chart depicting the method of the present invention for treating maladies within lumen, cavities, and tissues of the body.

FIG. 5 contains a flow chart depicting the method of the present invention for treating maladies within lumens, cavities, and tissues of the body. In order to make the foregoing description more concrete in the reader's mind, the method is described with reference to treating a malady of bone marrow, such as, but not limited to, osteomyelitis and/or leukemia. It should be noted, that any tissue, cavity, and/or lumen of the body may be substituted for bone marrow in the foregoing description. As indicated in Box 1, the method begins by first selecting the appropriate liquid to deliver to the bone marrow. Ideally the liquid chosen should provide a therapeutic benefit to the bone marrow such as, but not limited to, dissolving unwanted accretions, killing infectious organisms, arresting the growth of infectious organisms, killing cancerous cells, hindering the growth of cancerous cells, encouraging the growth of healthy cells, cleansing the bone marrow of infectious organisms, cleansing the bone marrow of diseased tissue, cleansing the bone marrow of necrotic tissue, or any combination thereof. Ideally the liquid chosen should not harm and/or hinder the growth of healthy tissue any more than necessary to achieve the intended therapeutic benefit. A biopsy of the bone marrow may assist a person utilizing the method of present the invention in selecting the appropriate liquid. Culturing the removed bone marrow may allow the user to identify the infectious microbe causing the malady to be treated. A biopsy of the bone marrow may also allow the user of the method of the present invention to identify the particular form of leukemia to be treated. Identifying the infectious microbe and/or particular leukemia present allows the user to select a liquid known and/or believed to be effective in treating the infection and/or leukemia present. Other manners of diagnosis and/or selection of an appropriate liquid are well known to those skilled in the healing arts and may be equally as effective.

In keeping with FIG. 5, after selecting an appropriate liquid, the user of the present invention, as depicted in Diamond 2, must then determine whether or not the creation of an orifice or plurality of orifices extending into the bone marrow is warranted. If an orifice in the form of a sore, wound, and/or fissure extending into the bone marrow is already present, creation of additional orifices may not be necessary. However, if no such orifice is present, then an orifice extending into the bone marrow must be created, as depicted in Box 3. Creating multiple orifices extending into the bone marrow enables the user of the present invention to deliver the chosen liquid into the bone marrow from multiple sites. Additionally, the creation of multiple orifices enables the user of the present invention to flush and/or wash the bone marrow to be treated. Injecting a liquid into the bone marrow with the present invention forces the injected liquid through the bone marrow and out at least one secondary orifice present. Flushing and/or washing the bone marrow may be advantageous when the goal of the treatment is to remove necrotic tissue, cleanse the bone marrow of infectious organisms, cleanse the bone marrow of diseased tissue, removal undesirable elements from the bone marrow, and/or any combination thereof. Orifices may be positioned at any position throughout the bone so long as they provide access to the bone marrow being treated.

As depicted in Box 4 of FIG. 5, orifices already present and/or created may be reinforced by implanting a cannula into the orifice. Implantation of a cannula into the orifice helps to prevent wound closure during the interval between successive treatments. Ideally, implanted cannulae should extend into the bone marrow. Once all orifices have been created and cannulae inserted, if any, the delivery device is completely assembled and prepared for operation, as depicted in Box 5, if not already done so. Assembling the delivery device comprises the steps of selecting and attaching an appropriate dampening grommet to the distal end of the ultrasound horn, filling the channel or channels within the ultrasound horn with the chosen liquid, or if a liquid supply is utilized filling a liquid supply with the chosen liquid and attaching said liquid supply to a channel running through the ultrasound horn, connecting said horn to an ultrasound transducer, connecting said transducer to a generator, and connecting said generator to a power supply. Once the device has been assembled, orifices created, and cannulae, if any, implanted, a seal is then formed between at least one orifice and the dampening grommet, as depicted in Box 6. Forming the seal may be done by inserting the grommet into the orifice, or cannula if present, such that a seal forms between the outer sides of the grommet and the inner sides of the orifice or cannula. Alternatively, pressing the dampening grommet against a region of the patient's skin encompassing said orifice, or cannula if present, may also be done to form a seal between the base of the dampening grommet and the orifice or cannula. If a cannula has been implanted and the cannula extends out of the patient's body, forming a seal between the dampening grommet and an orifice may be accomplished by sliding the grommet down the cannulla such that a seal forms between the inner sides of the grommet and the outer sides of the cannula. The ultrasound transducer is then activated, as depicted by Box 7. If a liquid supply is being utilized, following the activation of the ultrasound transducer the chosen liquid is dispensed into a channel within the ultrasound horn, as depicted in Box 8. Following the activation of the ultrasound transducer the chosen liquid is then delivered to the bone marrow for at least approximately five seconds, as depicted by Box 9. Increasing the duration of liquid delivery, however, may be necessary depending on the severity of the malady being treated. If multiple orifices are present, the user of the present invention may wish to collect, wipe away, or otherwise remove any fluid discharged from any secondary orifices, as depicted in Box 10, simultaneously with the delivery of the liquid to the bone marrow. Collecting discharged fluid in a sealed reservoir may lessen the possibly of contaminating and/or spreading the malady being treated into the surroundings of the treatment procedure.

In keeping with FIG. 5, following the completion of liquid delivery the ultrasound transducer is deactivated, as depicted in Box 11. The dampening grommet is then removed from orifices against which it is sealed. The orifices or cannulae, if any, should then be cleaned and covered, as depicted in Box 12. Methods of cleaning and covering such orifices and/or cannulae are well known to those skilled in the healing arts. The ultrasound liquid delivery device of the present invention should then be disassembled, as depicted in Box 13. Disposable portions of the present invention, which may comprise the dampening grommet, flexible hose, and/or fluid supply, should be disposed of, as depicted in Box 14. The remaining portions of the device should be cleaned and sterilized, as depicted in Box 15. Methods of cleaning and sterilizing such elements are well known to those skilled in the healing arts. The procedure depicted in FIG. 5 should be repeated daily for approximately 10 days, at least. However, depending on the severity of the malady to be treated, the period and/or frequency of treatment may need to be increased or could be decreased. After the final treatment session, any cannulae inserted should be removed.

It should be noted the sequence of steps described above and depicted in FIG. 5 is merely a suggested sequence. Other combinations and/or sequences of the enumerated steps may be equally effective and are within the scope of the present invention. It should also be noted that the above procedure is applicable for treating lumens, cavities and tissues, other than bone marrow, of the body.

Figure 6:
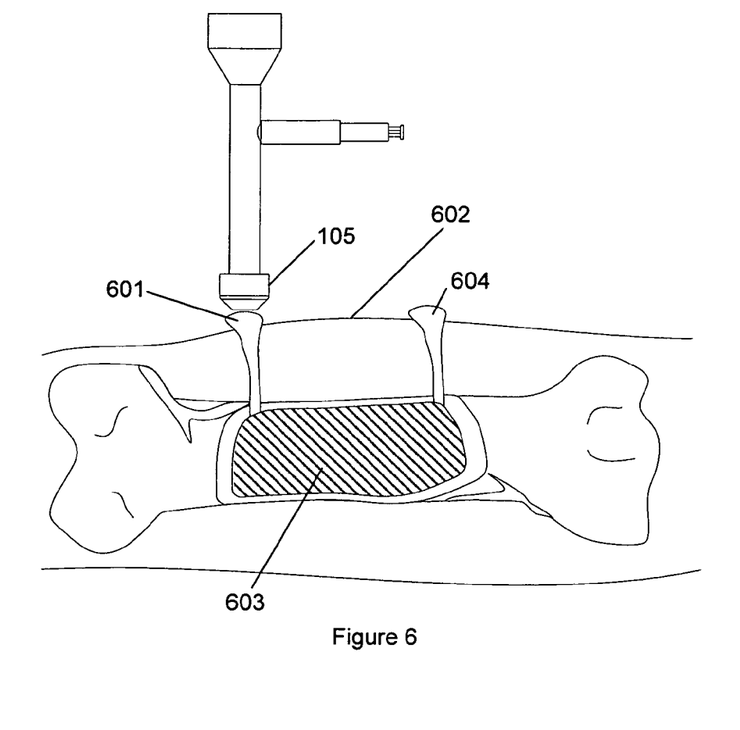
FIG. 6 is an illustration of the treatment of bone marrow with a delivery device.

Depicted in FIG. 6 is an illustration of the treatment of bone marrow with a delivery device. Grommet 105 is inserted into a cannula 601, extending from the surface of the patient's skin 602 to the bone marrow 603. Alternatively grommet 105 may be inserted into an orifice extending into the bone marrow 603. Cannula 604 is an optional additional cannula extending into the bone marrow which may serve as a point of egress for fluids within bone marrow and/or liquid delivered to the bone marrow. Cannula 604 may also serve as an additional orifice for liquid delivery.

Although specific embodiments and methods of use have been illustrated and described herein, it will be appreciated by those of ordinary skill in the art that any arrangement that is calculated to achieve the same purpose may be substituted for the specific embodiments and methods shown. It is to be understood that the above description is intended to be illustrative and not restrictive. Combinations of the above embodiments and other embodiments as well as combinations of the above methods and other methods will be apparent to those having skill in the art upon review of the present disclosure. The scope of the present invention should be determined with reference to the appended claims, along with the full scope of equivalents to which such claims are entitled.

I claim:

1. A method of treating and/or cleansing a treatment area accessible through an orifice comprising the steps of:
   a. Forming a seal between a dampening grommet, capable of blocking the transmission of vibrations, attached to the distal end of an ultrasound horn and an orifice or plurality of orifices leading into the treatment area
   b. Dispensing a liquid to be delivered to the treatment area into a channel running at least partially through said ultrasound horn;
   c. Delivering ultrasound energy to said liquid within the channel by inducing the horn to vibrate at a frequency between approximately 15 kHz and approximately 40 MHz, wherein said ultrasound energy accelerates said liquid;
   d. Allowing said liquid to be ejected from the distal end of the grommet, and
   e. Injecting said liquid ejected from said grommet into the orifice or plurality of orifices extending into the treatment area.

2. The method of claim 1, further characterized by said ultrasound energy delivery to said liquid delivering ultrasound energy to the treatment area.

3. The method of claim 1, further characterized by said ultrasound energy delivery to said liquid inducing cavitations within the treatment area.

4. The method of claim 1, further comprising the step of creating said orifice.

5. The method of claim 1, further comprising the step of inserting a cannula into said orifice.

6. The method of claim 5, further comprising the step of removing said cannula.

7. The method of claim 5, further comprising the step of covering said cannula.

8. The method of claim 1, further characterized by said injection of liquid occurring for at least approximately 5 seconds.

9. The method of claim 1, further comprising the step of covering said orifice.

10. The method of claim 1 further characterized by said induced vibrations having an amplitude between approximately 1 micron and approximately 250 microns.

* * * * *